(12) United States Patent
Wholey et al.

(10) Patent No.: US 7,322,958 B2
(45) Date of Patent: Jan. 29, 2008

(54) APPARATUS FOR THROMBOEMBOLIC PROTECTION

(76) Inventors: Mark H. Wholey, 816 Woodland Ave., Oakmont, PA (US) 15139; Michael Wholey, 19407 Strauss La., San Antonio, TX (US) 78256

( * ) Notice: Subject to any disclaimer, the term of this patent is extended or adjusted under 35 U.S.C. 154(b) by 490 days.

(21) Appl. No.: 10/329,585

(22) Filed: Dec. 26, 2002

(65) Prior Publication Data
US 2003/0158516 A1    Aug. 21, 2003

Related U.S. Application Data

(60) Provisional application No. 60/344,168, filed on Dec. 27, 2001.

(51) Int. Cl.
*A61M 29/00* (2006.01)
(52) U.S. Cl. .................. 604/102.01; 604/96.01
(58) Field of Classification Search .. 604/95.03–95.04, 604/96.01, 97.01, 98.01, 103.05, 109, 102.01, 604/102.03, 103.14, 164.13, 506–510, 915–920, 604/97.07; 606/192–200; 600/585
See application file for complete search history.

(56) References Cited

U.S. PATENT DOCUMENTS

| | | | |
|---|---|---|---|
| 4,024,873 A | 5/1977 | Antoshkiw et al. | |
| 4,351,341 A | 9/1982 | Goldberg et al. | |
| 4,723,549 A | 2/1988 | Wholey et al. | |
| 4,873,978 A | 10/1989 | Ginsburg | |
| 5,011,488 A | 4/1991 | Ginsburg | |
| 5,053,008 A | 10/1991 | Bajaj | |
| 5,167,239 A * | 12/1992 | Cohen et al. | 600/585 |
| 5,256,144 A * | 10/1993 | Kraus et al. | 604/96.01 |
| 5,549,626 A | 8/1996 | Miller et al. | |
| 5,649,908 A * | 7/1997 | Itoh | 604/96.01 |

(Continued)

OTHER PUBLICATIONS

"Prevention: Latest stents used for the treatment of stenosis", at http://my.cardiovalens.com/featured/featuredisplay.asp?featureid=101 (downloaded on Nov. 26, 2003), undated.

(Continued)

*Primary Examiner*—Kevin C. Sirmons
*Assistant Examiner*—Andrew Gilbert
(74) *Attorney, Agent, or Firm*—Matthew W. Gordon, Esq.; Alan G. Towner, Esq.; Pietragallo Bosick & Gordon, LLP

(57) ABSTRACT

A catheter apparatus captures thromboembolic material in the arterial and venous circulation. The apparatus includes an inner hollow tube and an outer hollow tube in sliding engagement with the inner hollow tube. A radially expandable segment, such as an inflatable balloon, is attached near the distal end of the catheter. One end portion of the balloon is attached to the inner tube and the other end portion is attached to the outer tube. When the catheter is advanced through a vessel to be treated, the balloon is deflated and the outer tube is slidably advanced to a storage position so that the balloon compactly surrounds the catheter. When the catheter is in place within the vessel, the outer tube is slidably advanced to a treatment position and the balloon is inflated. As the vessel is treated, the inflated balloon captures and contains thromboembolic particles that may be released, and the particles are suctioned out of the patient through apertures located in the outer hollow tube proximal to the balloon.

26 Claims, 6 Drawing Sheets

U.S. PATENT DOCUMENTS

| | | | |
|---|---|---|---|
| 5,674,198 A * | 10/1997 | Leone | 604/101.05 |
| 5,695,519 A | 12/1997 | Summers et al. | |
| 5,766,151 A * | 6/1998 | Valley et al. | 604/103.07 |
| 5,769,816 A | 6/1998 | Barbut et al. | |
| 5,779,716 A | 7/1998 | Cano et al. | |
| 5,814,064 A | 9/1998 | Daniel et al. | |
| 5,827,324 A | 10/1998 | Cassell et al. | |
| 5,833,650 A | 11/1998 | Imran | |
| 5,853,420 A | 12/1998 | Chevillon et al. | |
| 5,908,435 A | 6/1999 | Samuels | |
| 5,910,154 A | 6/1999 | Tsugita et al. | |
| 5,911,734 A | 6/1999 | Tsugita et al. | |
| 5,954,745 A | 9/1999 | Gertler et al. | |
| 6,022,336 A | 2/2000 | Zadno-Azizi et al. | |
| 6,027,520 A | 2/2000 | Tsugita et al. | |
| 6,042,598 A | 3/2000 | Tsugita et al. | |
| 6,059,814 A | 5/2000 | Ladd | |
| 6,096,053 A | 8/2000 | Bates | |
| 6,135,991 A | 10/2000 | Muni et al. | |
| 6,152,946 A | 11/2000 | Broome et al. | |
| 6,165,200 A | 12/2000 | Tsugita et al. | |
| 6,171,327 B1 | 1/2001 | Daniel et al. | |
| 6,179,859 B1 | 1/2001 | Bates et al. | |
| 6,245,089 B1 | 6/2001 | Daniel et al. | |
| 6,290,710 B1 | 9/2001 | Cryer et al. | |
| 6,336,934 B1 | 1/2002 | Gilson et al. | |
| 6,361,545 B1 | 3/2002 | Macoviak et al. | |
| 6,398,773 B1 | 6/2002 | Bagaoisan et al. | |
| 6,443,926 B1 * | 9/2002 | Kletschka | 604/96.01 |
| 6,454,741 B1 | 9/2002 | Muni et al. | |
| 6,485,456 B1 * | 11/2002 | Kletschka | 604/96.01 |

OTHER PUBLICATIONS

Medtronic AVE information sheet at www.medtronicave.com (downloaded on Nov. 26, 2003), undated.

"Distal Protection Devices" article at www.medtronic.com (downloaded on Nov. 26, 2003), undated.

"What is a Coronary Distal Protection System?" article at www.medtronic.com (downloaded on Nov. 26, 2003), undated.

* cited by examiner

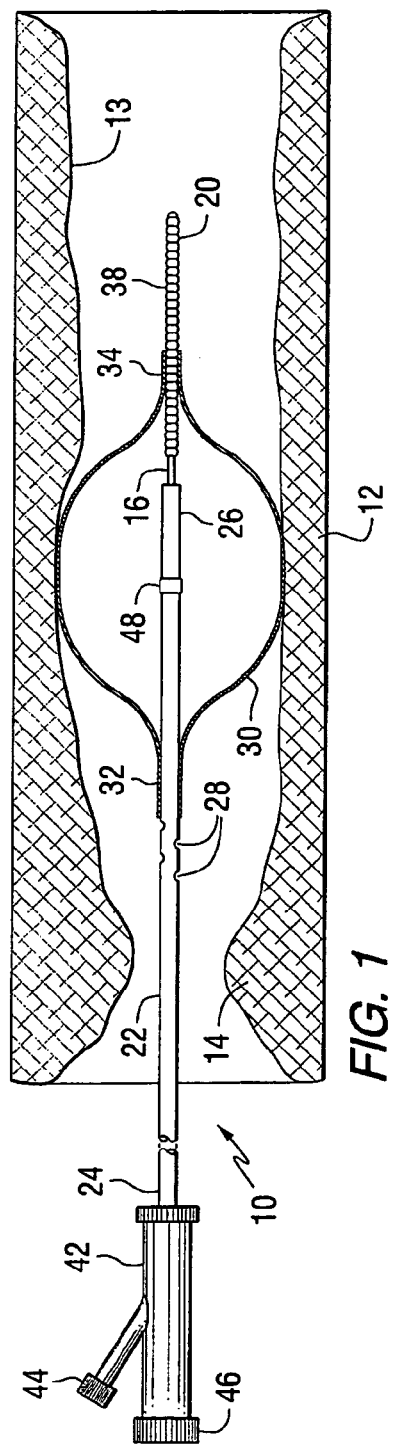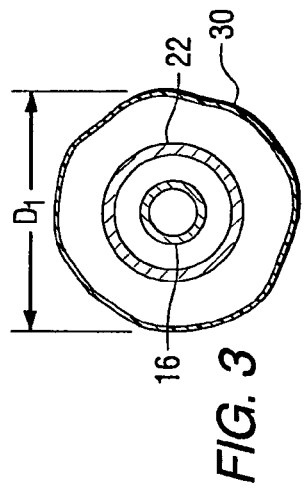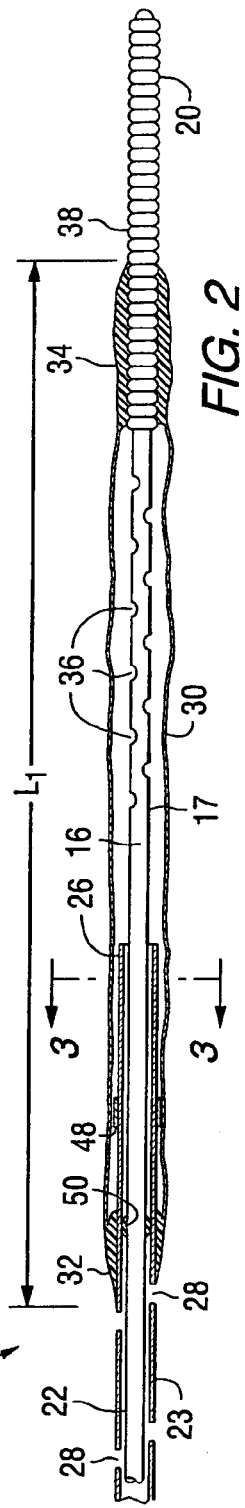

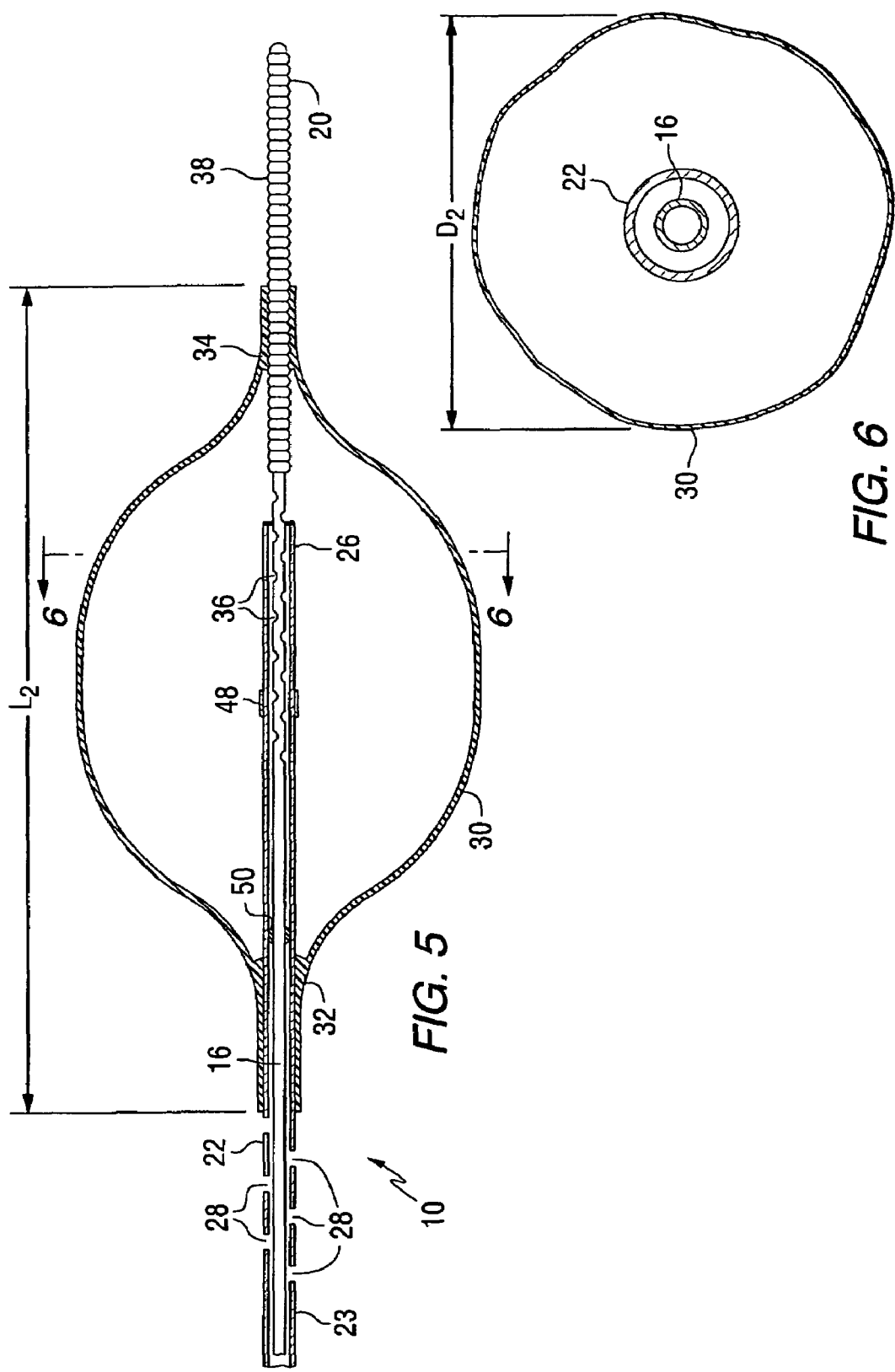

APPARATUS FOR THROMBOEMBOLIC PROTECTION

CROSS-REFERENCE TO RELATED APPLICATION

This application claims the benefit of U.S. Provisional Patent Application Ser. No. 60/344,168 filed Dec. 27, 2001.

FIELD OF THE INVENTION

The present invention relates to thromboembolic protection, and more particularly relates to an instrument including a radially expandable segment mounted on a tube such as a guidewire for thromboembolic protection. Methods of utilizing the instrument to provide thromboembolic protection are also provided.

BACKGROUND INFORMATION

It is common practice today to open occluded (i.e., blocked) or stenotic (i.e., narrowed) blood vessels by inserting a guide wire and then a catheter carrying a balloon shaped segment and inflating the balloon, which exerts a radial force to press stenosis outward against the wall of the blood vessel. This procedure is called balloon angioplasty. Frequently, an implantable metallic stent will also be used to provide greater radial strength at the stenotic portion of the blood vessel, and to provide longer-term patency.

During the balloon angioplasty procedure and stent placement at the stenotic lesion, there may exist the risk of dislodging fragments of plaque, thrombus (blood clots) and/or other material. These fragments may become dislodged from the stenotic lesion when the balloon segment is inflated. If the lesion involves arterial circulation, then the dislodged particles could flow into smaller vessels in the brain, other organs, or extremities, resulting in disastrous complications. Likewise, if the lesions involve the venous circulation, then the dislodged fragments could flow into the heart and lungs, possibly resulting in the demise of the patient.

Embolic protection devices are typically used to provide protection from such dislodged fragments of plaque and thrombus. These protection devices may consist of a radially expandable segment, such as a balloon, attached near the end of a tube or guidewire. The guidewire with the balloon may be advanced across a stenotic lesion with the balloon in an unexpanded state, and then the balloon may be expanded in an area of the blood vessel past the stenotic lesion or downstream therefrom. When expanded, the balloon can capture and contain dislodged particles. The captured particles may then be removed with various known methods, such as aspiration. When the procedure is completed, the balloon may be deflated and the tube and the deflated balloon may be removed from the patient.

There are disadvantages to such devices. If the targeted blood vessel is tortuous and/or the lesion of the blood vessel to be treated contains a relatively high-grade stenosis, it is often difficult to pass the balloon portion of the catheter through the vessel and into position, even if the balloon portion is deflated. These same problems often arise when the catheter is removed from the patient after the procedure is completed. Even in a deflated position, the crossing profile of the balloon segment may be such that scraping and/or focal dissection of the blood vessel wall may occur as the balloon segment is passed through the diseased portion of the blood vessel, thereby dislodging and releasing embolic material and other particles into the bloodstream. Likewise, the deflated balloon segment of the catheter may often become snagged or caught on the edge of a stent as the balloon segment attempts to pass through such a newly placed stent when the catheter is removed from the patient.

The present invention has been developed in view of the foregoing disadvantages, and to address other deficiencies of the prior art.

SUMMARY OF THE INVENTION

The present invention relates to a catheter apparatus and method for collecting blood clots, pieces of plaque, and other material that may be accidentally dislodged during interventional procedures in the human vasculature, such as arterial and venous angioplasty and stent placement. The apparatus includes a radially expandable segment, such as an inflatable balloon, which captures and contains the dislodged fragments. The fragments can then be suctioned through the apparatus and removed from the patient.

The apparatus includes an inner hollow tube and an outer hollow tube in sliding engagement with the inner hollow tube. One end portion of the inflatable balloon is attached to the inner tube and the other end portion is attached to the outer tube. When the apparatus is advanced through a vessel to be treated, the balloon is deflated and the outer tube is slidably advanced to a storage position so that the balloon compactly surrounds the apparatus. When the apparatus is in place within the vessel, the outer tube may be slidably advanced to a treatment position, and the balloon may be inflated.

In one embodiment of the invention, the apparatus also serves a dual purpose as a guidewire. Once the distal end of the apparatus is advanced past the portion of the blood vessel to be treated, such as a stenotic lesion, the operator may use the apparatus to advance various coaxial catheters and devices into position to treat the lesion. Balloon catheters, stent delivery systems, intravascular ultrasound catheters and other interventional systems can be advanced over the present apparatus.

An aspect of the present invention is to provide an apparatus for capturing and retrieving embolic material from a blood vessel including a first hollow tube having a proximal end and a distal end, wherein the distal end is insertable into the vessel, a second hollow tube coaxially and slidably positioned over the first hollow tube, wherein a wall of the second hollow tube includes a plurality of apertures structured and configured for retrieving the embolic material, and a radially expandable segment expandable from a deflated position to an inflated position in contact with an inner wall of the blood vessel structured and configured for capturing the embolic material to be retrieved, wherein a proximal portion of the radially expandable segment is attached to the second hollow tube, and a distal portion of the radially expandable segment is attached adjacent the distal end of the first hollow tube.

Another aspect of the present invention is to provide an apparatus for capturing and retrieving embolic material from a blood vessel including a first hollow tube having a proximal end and a distal end, wherein the distal end is insertable into the vessel, a second hollow tube coaxially positioned over the first hollow tube, wherein a wall of the second hollow tube includes a plurality of apertures structured and configured for retrieving the embolic material, a radially expandable segment attached to the first hollow tube and the second hollow tube and structured and configured for capturing the embolic material to be retrieved, and means for compactly surrounding at least a portion of the first hollow tube and at least a portion of the second hollow tube with the radially expandable segment.

A further aspect of the present invention is to provide a method for capturing and retrieving embolic material from a blood vessel including the steps of inserting a catheter into the blood vessel, wherein the catheter comprises a first hollow tube having a proximal end and a distal end, a second hollow tube coaxially and slidably positioned over the first hollow tube and advanced towards the proximal end of the first hollow tube in a storage position, wherein a wall of the second hollow tube includes a plurality of apertures structured and configured for retrieving the embolic material, and a radially expandable segment, wherein a proximal portion of the radially expandable segment is attached to the second hollow tube and a distal portion of the radially expandable segment is attached adjacent the distal end of the first hollow tube, guiding the radially expandable segment past a portion of the blood vessel to be treated, sliding the second hollow tube to a treatment position, inflating the radially expandable segment, treating the blood vessel, deflating the radially expandable segment and sliding the second hollow tube to the storage position, and removing the catheter from the blood vessel.

Another aspect of the present invention is to provide a method of capturing and retrieving embolic material from a blood vessel including the steps of inserting a catheter into the blood vessel, wherein the catheter comprises a first hollow tube having a proximal end and a distal end, a second hollow tube coaxially and slidably positioned over the first hollow tube and advanced towards the proximal end of the first hollow tube in a storage position, wherein a wall of the second hollow tube includes a plurality of apertures structured and configured for retrieving the embolic material, and a radially expandable segment, wherein a proximal portion of the radially expandable segment is attached to the second hollow tube and a distal portion of the radially expandable segment is attached adjacent the distal end of the first hollow tube, guiding the radially expandable segment past a portion of the blood vessel to be treated, sliding the second hollow tube to a treatment position, inflating the radially expandable segment, treating the blood vessel by advancing the catheter in a proximal direction, wherein the inflated radially expandable segment passes through the portion of the blood vessel to be treated, thereby capturing embolic material, removing the captured embolic material through the apertures of the second hollow tube to a location outside of the blood vessel, deflating the radially expandable segment, and removing the catheter from the blood vessel.

These and other aspects of the present invention will be more apparent from the following description.

BRIEF DESCRIPTION OF THE DRAWINGS

FIG. 1 is a longitudinal side view of a catheter apparatus for thromboembolic protection in accordance with an embodiment of the present invention.

FIG. 2 is a partially schematic longitudinal sectional view of the apparatus of FIG. 1, with the outer tube in a storage position and the balloon segment in a deflated position.

FIG. 3 is a sectional view taken along the line 3-3 of the apparatus of FIG. 2.

FIG. 5 is a partially schematic longitudinal sectional view of the catheter of FIG. 1, with the outer tube in a treatment position and the balloon segment in an inflated position.

FIG. 6 is a sectional view taken along the line 6-6 of the catheter of FIG. 5.

DETAILED DESCRIPTION OF THE INVENTION

Figure 4:
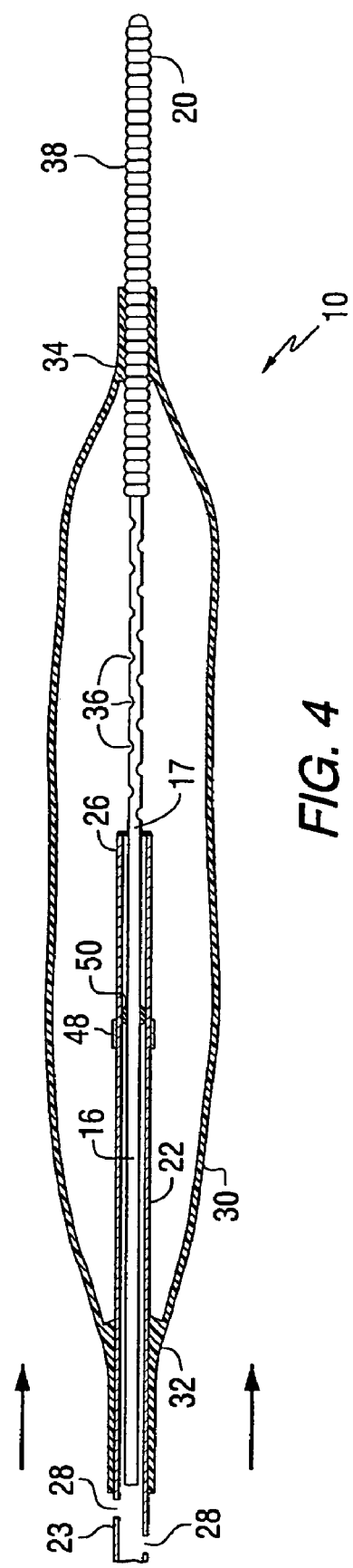
FIG. 4 is a partially schematic longitudinal sectional view of the catheter of FIG. 1.

The apparatus of the present invention includes a catheter with a radially expandable segment, such as an inflatable balloon, disposed near the distal end of the catheter. The apparatus may be inserted into a blood vessel of a patient, and the balloon segment may be inflated to capture and contain embolic material before, during, and/or after treatment of the blood vessel. As used herein, "treatment" of a blood vessel includes interventional procedures, such as transluminal angioplasty or stenting. As used herein, "embolic material" includes plaque, thrombus, thromboembolic fragments, or any other material that may be affixed to a blood vessel wall or dislodged from a blood vessel wall and released into the blood stream during treatment of the vessel. The apparatus also includes apertures for removing the captured embolic material from the blood vessel.

In the embodiment described herein, the apparatus includes an inner hollow tube and an outer hollow tube coaxially and slidably positioned over the inner hollow tube. A portion of the inner hollow tube may extend distally in length beyond the outer hollow tube, and one end portion of the inflatable balloon is attached to the inner tube and the other end portion of the balloon is attached to the outer tube. When the apparatus is being advanced through a vessel to be treated, the balloon is deflated and the outer tube may be slidably advanced to a storage position so that the balloon compactly surrounds the apparatus. As used herein, "storage position" means that the outer tube is advanced towards the proximal end of the inner hollow tube so that the balloon segment compactly surrounds the apparatus. As used herein, "compactly surrounds" means that the balloon segment is drawn down around portions of the inner and/or outer hollow tubes. The balloon segment may contact at least a portion of the inner tube and/or at least a portion of the outer tube. In one embodiment, the balloon segment may be placed in tension when the second outer tube is in the storage position.

When the balloon segment is placed in tension, the tensile force may be sufficient to elongate the elastic material of the balloon segment. The balloon segment may be elongated, for example, from about 0.1 to about 50 percent, typically from about 0.5 to about 20 percent.

When the apparatus is in the appropriate place within the vessel and the balloon segment is downstream from the portion of the vessel to be treated, the outer tube may be slidably advanced to a treatment position, and the balloon may be inflated. As used herein, "treatment position" means that the outer tube is advanced towards the distal end of the inner hollow tube so that the balloon segment may be freely inflated against the inner wall of the vessel to an appropriate diameter to properly capture and contain embolic material. As the outer tube is advanced to the treatment position, any tension applied to the balloon segment is released and the balloon segment may begin to bulge outward before the balloon is inflated. The outer tube may be slidably moved between the storage position and the treatment position, and vice-versa.

In one embodiment, the outer tube may be manually moved to the storage position or the treatment position by an operator as the balloon is inflated or deflated. In another embodiment, as the balloon is inflated the outer hollow tube may automatically slide to the treatment position as a result of the balloon expanding.

In a preferred embodiment, the present apparatus may also serve as a guidewire which allows the operator to coaxially advance various instruments and catheters, such as balloon catheters and stent systems, to the portion of the blood vessel that requires treatment.

As shown in the embodiment of FIGS. 1-9, the catheter apparatus 10 of the present invention includes a first hollow tube 16 having a proximal end 18 and a distal end 20 which is insertable into a blood vessel 12 through an incision (not shown) upstream of a treatment area 14 of the blood vessel 12.

The first hollow tube 16 may have an inner diameter of from about 0.05 mm to about 1.5 mm, preferably from about 0.25 mm to about 0.9 mm. In a particularly preferred embodiment the first hollow tube may have an inner diameter of about 0.25 mm. The first hollow tube 16 may have an outer diameter of from about 0.05 mm to about 2 mm, preferably from about 0.25 mm to about 1 mm. In a particularly preferred embodiment the first hollow tube may have an outer diameter of about 0.6 mm.

The apparatus 10 also includes a second hollow tube 22 having a proximal end 24 and a distal end 26. The second tube 22 is coaxially and slidably positioned over the first hollow tube 16. The second hollow tube 22 may be slidably moved between the storage position and the treatment position, and vice-versa. FIG. 4 shows the second hollow tube 22 sliding from the storage position to the treatment position. The second hollow tube 22 may have an inner diameter of from about 0.25 mm to about 2.3 mm, preferably from about 0.25 mm to about 0.5 mm. In a particularly preferred embodiment the second hollow tube may have an inner diameter of about 0.3 mm. The second hollow tube 22 may have an outer diameter of from about 0.3 mm to about 2.5 mm, preferably from about 0.35 mm to about 0.9 mm. In a particularly preferred embodiment the second hollow tube may have an outer diameter of about 0.65 mm.

The first hollow tube 16 and the second hollow tube 22 may be made out of any suitable material, such as polyethylene, polyamide, polytetraflurethylene, or any other polyester compounds. As most clearly shown in FIGS. 2, 4 and 5, a first sealing means, such as an O-ring 50, may substantially surround the first hollow tube 16 at a location between inflation apertures 36 and aspiration apertures 28. Preferably, the O-ring 50 is mounted to the first hollow tube 16 near where a proximal portion 32 of the balloon 30 attaches to the second hollow tube 22. The second hollow tube 22 may slide over the O-ring 50. Alternatively, the O-ring 50 may be attached to the interior of the second hollow tube 22, and the first hollow tube 22 and the O-ring 50 may slide in combination over the first hollow tube 16. O-ring 50 functions to create a seal between the inflation apertures 36 and the aspiration apertures 28.

The apparatus 10 includes a radially expandable segment, such as an inflatable balloon segment 30, mounted near the distal end of the apparatus. The inflatable balloon segment 30 may be made out of any suitable material, such as but not limited to, PET, polyethylene, polyamide, or PTFE. A portion of the first hollow tube 16 may extend distally in length beyond the second hollow tube 22, and a proximal portion 32 of the balloon 30 may be attached near the distal end 26 of the second hollow tube 22 and a distal portion 34 of the balloon 30 may be attached adjacent the distal end 20 of the first hollow tube 16. The distal portion 34 of the balloon 30 may also be attached to the flexible material 38, as illustrated in FIGS. 1, 2, 4 and 5. The proximal portion 32 and the distal portion 34 of the inflatable balloon 30 may be attached to the catheter apparatus 10 with any suitable securing means, such as a medical grade glue.

In a preferred embodiment of the invention, as the apparatus 10 is being advanced through the vessel 12 to be treated, the balloon segment 30 is deflated and the second hollow tube 22 may be slidably and coaxially advanced to the storage position so that the balloon compactly surrounds at least a portion of the first hollow tube and at least a portion of the second hollow tube. FIG. 2 illustrates the second hollow tube 22 in the storage position. In the storage position, the balloon segment 30 compactly surrounds the first and second tubes 16 and 22, and may be placed in tension.

When the balloon segment 30 is in the deflated position and the second hollow tube 22 is in the storage position, the balloon segment 30 may have a diameter $D_1$ of from about 0.8 mm to about 3 mm, preferably from about 0.85 mm to about 1.4 mm. In a particularly preferred embodiment, the balloon segment 30 has a diameter $D_1$ of about 0.85 mm.

When the second hollow tube 22 is in the storage position, the deflated balloon segment 30 may have a length $L_1$ of from about 0.25 cm to about 8 cm, preferably of from about 1 cm to about 4 cm. In a particularly preferred embodiment, the balloon segment 30 may have a length $L_1$ in the deflated position of about 2 cm.

The balloon segment 30 maintains a low profile as it passes through the vessel 12. When the apparatus 10 is in the appropriate position to facilitate treatment of the vessel 12 and the balloon segment 30 has been advanced downstream from the treatment area 14 of the vessel 12, the second hollow tube 22 may be coaxially and slidably advanced to the treatment position and the balloon 30 may be inflated against the inner wall 13 of the vessel 12 to an appropriate diameter to effectively capture and contain embolic material that may be released when the vessel is treated. Inflation apertures 36 located in the wall 17 of the first hollow tube 16 allow for the inflatable balloon segment 30 to be inflated and/or deflated. FIGS. 2-7 show that a wall 23 of the second hollow tube 22 also includes apertures 28. These aspiration apertures 28 are preferably located proximal to the balloon segment 30. As the embolic material is captured and contained with the expanded balloon segment 30, suction may be used to pull the embolic material through the apertures 28 into the second hollow tube 22, and out of the patient.

When the second hollow tube 22 is in the treatment position, the balloon segment 30 may be inflated to a diameter $D_2$ of from about 2 mm to about 30 mm, preferably to a diameter of from about 3 mm to about 11 mm. In a particularly preferred embodiment, the balloon segment 30 may be inflated to a diameter $D_2$ of about 6 mm. A ratio of the inflated diameter $D_2$ to the deflated diameter $D_1$ may be defined as $D_2:D_1$. $D_2:D_1$ may range from about 2.5:1 to about 10:1, preferably from about 3.5:1 to about 8:1. In a particularly preferred embodiment, $D_2:D_1$ may be about 7:1.

When the second hollow tube 22 is in the treatment position, the balloon segment 30 may have a length $L_2$ of from about 0.25 cm to about 4 cm, preferably of from about 0.5 cm to about 2 cm. In a particularly preferred embodiment, the balloon segment 30 may have a length $L_2$ in the inflated position of about 1 cm.

Figure 7:
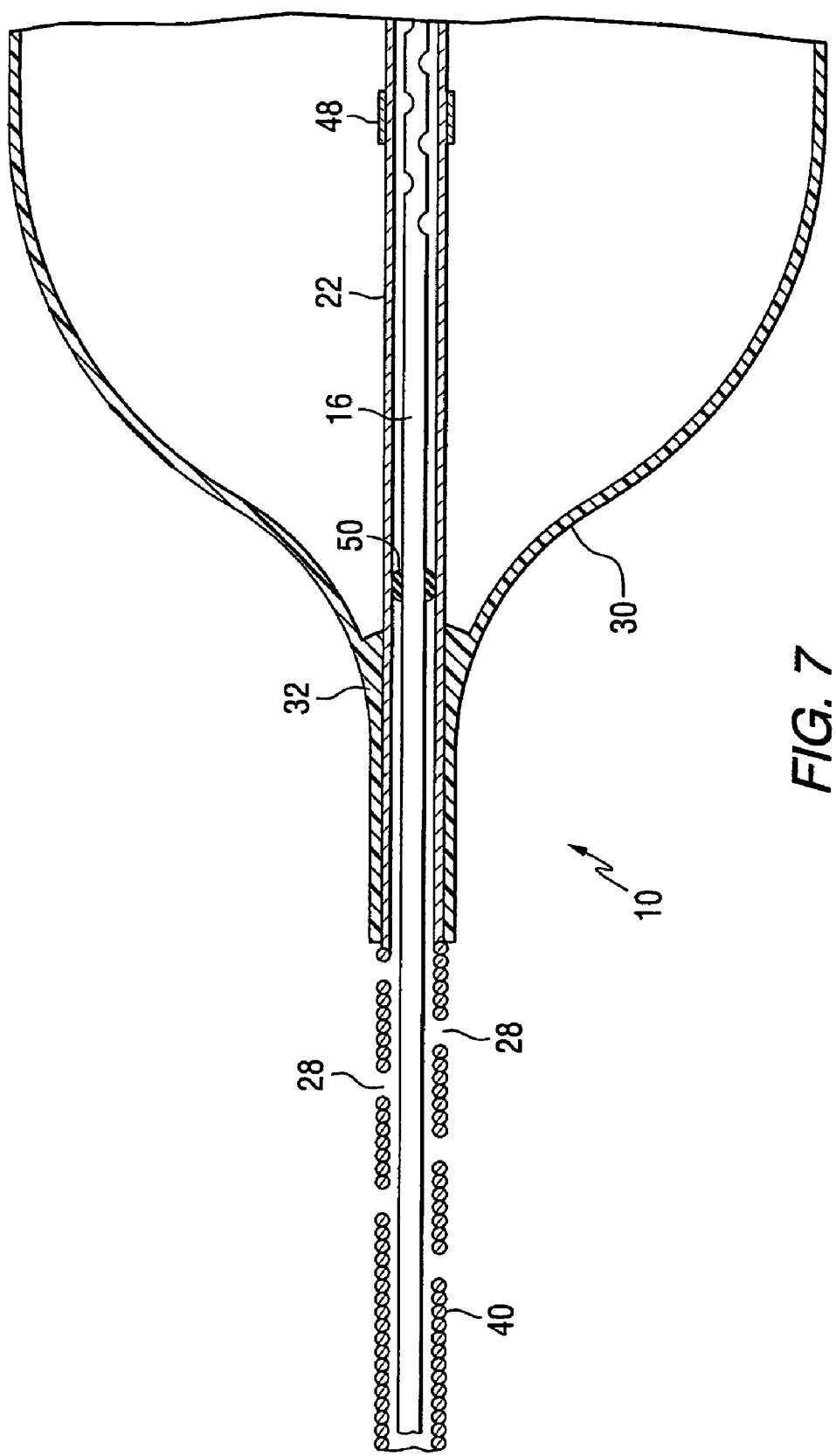
FIG. 7 is a partially schematic longitudinal sectional view of the catheter of FIG. 1.

At least a portion of the second hollow tube 22 may include a guidewire, and the guidewire may be a coiled guidewire 40 as illustrated in FIG. 7. The distal portion of the first hollow tube 16 may include a flexible material 38 which is preferably soft and torquable so that it can easily be inserted into the vessel 12. This flexible material 38 may be optionally coated or constructed with a material of higher atomic density to aid in visualizing the distal portion of the first hollow tube 16, for instance, under fluoroscopy. The catheter 10 may also include radiopaque or metallic markers to aid in positioning the catheter 10 within the vessel 12, such as marker 48 mounted, for example, on the second hollow tube 22 as shown in FIG. 2.

In one embodiment, the balloon segment 30 may be placed in tension when the second hollow tube 22 is advanced to the storage position. Placing the balloon segment 30 in tension maintains a low profile of the balloon segment 30. Tension in the balloon segment 30 may be achieved and maintained, for example, by frictional engagement between the first hollow tube 16 and a sealing means, such as the O-ring 50, if the O-ring 50 is mounted on the interior of the second hollow tube 22 as previously described herein. Alternatively, frictional engagement may be achieved between the second hollow tube 22 and the O-ring 50 if the O-ring is mounted on the exterior of the first hollow tube 16, as also previously described herein.

Figure 8:
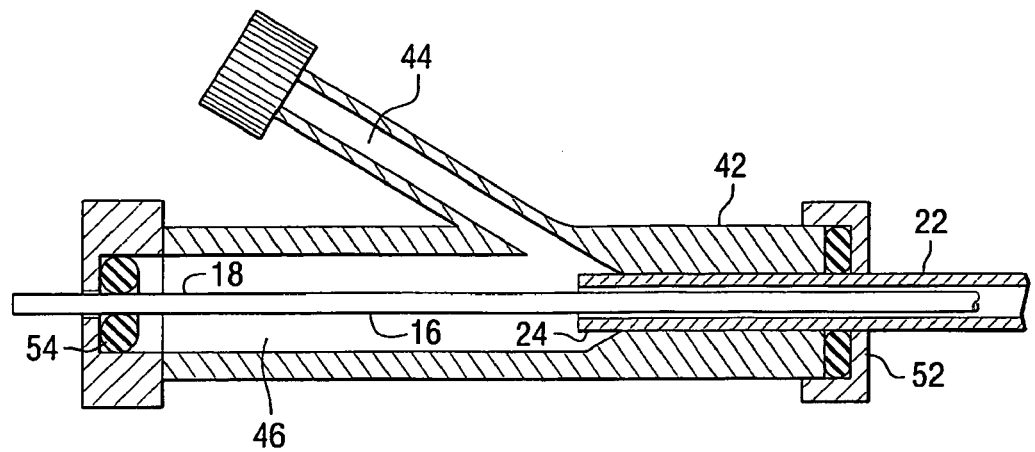
FIG. 8 is a partially schematic longitudinal sectional view of a proximal end of the catheter apparatus of FIG. 1.
Figure 9:
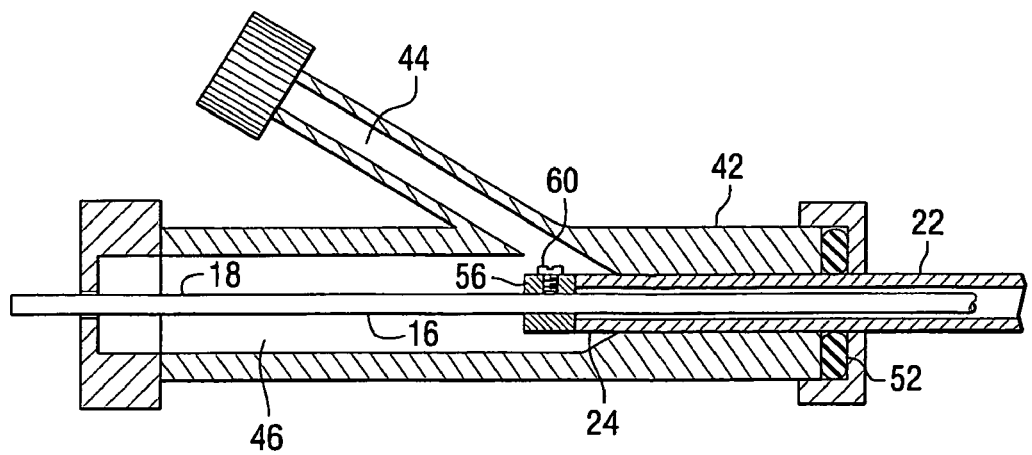
FIG. 9 is a partially schematic longitudinal sectional view of a proximal end of the catheter apparatus of FIG. 1.
Figure 10:
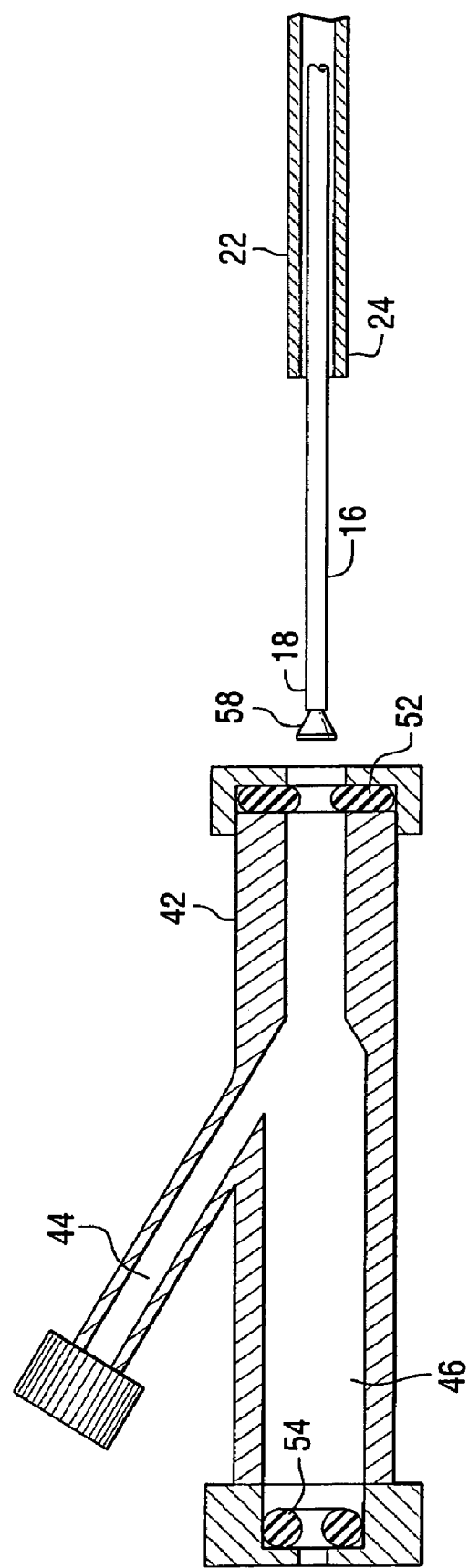
FIG. 10 is a partially schematic longitudinal sectional view of a proximal end of the catheter apparatus of FIG. 1.

Tension in the balloon segment 30 may also be achieved and maintained by the operator of the catheter apparatus. The operator may grasp and slide the second hollow tube 22 to the storage position while maintaining the position of the first hollow tube 16, thereby elongating the balloon 30 and placing the balloon in tension. The operator may also use a hub 42 as shown in FIGS. 8-10 to slide the second hollow tube. The balloon 30 may remain in tension until the operator releases the grasp on the second hollow tube 22.

In another embodiment, a latch, keeper, detent mechanism or the like (not shown) may be used to hold the second hollow tube 22 in the storage position and maintain tension on the balloon segment 30. For example, a keeper (not shown) may be mounted on the hub 42 of the apparatus 10 shown in FIGS. 8-10, and it may keep the second hollow tube 22 in the storage position with respect to the first hollow tube and maintain tension on the balloon segment 30.

As illustrated in FIGS. 8-10, the catheter apparatus 10 includes a hub 42 attached to the proximal end 18 of the first hollow tube 16 and the proximal end 24 of the second hollow tube 22. In a preferred embodiment, the hub 42 is removable from the catheter 10 to allow treatment devices to be coaxially advanced along the second hollow tube 22. When attached to the apparatus 10, the hub 42 may function as an actuator for sliding the second hollow tube 22 from the storage position to the treatment position, and vice-versa.

As illustrated in FIGS. 8-10, the hub 42 contains a first port 44 in flow communication with the second hollow tube 22 for supplying the second tube with suction for aspirating captured embolic material. The captured embolic material may also be removed from the patient via the first port 44. The hub 42 also contains a second port 46 for supplying materials for inflating or deflating the inflatable balloon 30 via the apertures 36, such as but not limited to, various gases and liquids. As illustrated in FIG. 10, a plug or stopper 58 may be used to maintain the balloon 30 in the inflated position by keeping the gases or liquids from leaking out.

FIG. 8 shows that the first hollow tube 16 passes through a sealing means, such as an O-ring 54 located within the second port 46, and then preferably protrudes from the second port 46. In one embodiment, a needle or a syringe may be used for supplying the materials to the first tube 16 for inflating or deflating the balloon 30. As also shown in FIG. 7, the second hollow tube 22 is surrounded by a sealing means, such as O-ring 52, as it enters the hub 42.

FIG. 9 shows that the O-ring 54 may be removed, and a small tubular member 56 may be placed over the first hollow tube 16 and adjacent to the proximal end 24 of the second hollow tube 22 to keep ensure that the second hollow tube 22 remains in the treatment position when the balloon is inflated. The tubular member 56 may be secured in place with any suitable means, such as a setscrew 60.

The catheter apparatus 10 may be used to provide embolic protection as follows: The apparatus 10 may be inserted into a blood vessel 12 to be treated, with the balloon segment 30 in the deflated position and the second hollow tube 22 in the storage position. The apparatus 10 may be guided through the vessel 12 until the balloon segment 30 passes through the treatment area 14 of the blood vessel 12. The second hollow tube 22 may then be distally advanced to the treatment position and balloon segment 30 may be inflated against the inner wall 13 of the blood vessel 12 via the inflation apertures 36. A treatment device may then be advanced along the second hollow tube 22, such as a balloon catheter or a stent delivery system, and the treatment area 14 of the blood vessel 12 may be treated. The inflated balloon 30 will capture and contain any embolic material that may be dislodged from the vessel 12 before, during, and/or after the vessel 12 is treated, and the captured embolic material may be aspirated through the aspiration apertures 28, into the second hollow tube 22, and out of the patient via the first port 44. The balloon segment 30 may then be deflated, the second hollow tube 22 may be advanced proximally back to the storage position, and the catheter apparatus 10 may be removed from the blood vessel 12.

In another embodiment of the present invention, the catheter apparatus 10 may also be used as a treatment device to treat a blood vessel. The apparatus 10 may be inserted into a blood vessel 12 to be treated, with the balloon segment 30 in the deflated position and the second hollow tube 22 in the storage position. The apparatus 10 may be guided through the vessel 12 until the balloon segment 30 passes through the treatment area 14 of the blood vessel 12. The second hollow tube 22 may then be distally advanced to the treatment position and balloon segment 30 may be inflated against the inner wall 13 of the blood vessel 12 via the inflation apertures 36. With the balloon segment 30 still in the inflated position, the catheter 10 may be proximally advanced through the vessel 12, so that the expanded balloon 30 passes back through the treatment area 14 of the vessel 12. As the balloon 30 passes through the treatment area 14, embolic material attached to the inner wall 13 of the vessel 12 will be removed and captured by the balloon 30. Loose embolic material in the vessel 12 will be captured as well. The captured embolic material may then be aspirated through the aspiration apertures 28, into the second hollow tube 22, and out of the patient via the first port 44. The balloon segment 30 may then be deflated, the second hollow tube 22 may be advanced proximally back to the storage position, and the catheter apparatus 10 may be removed from the blood vessel 12.

Whereas particular embodiments of this invention have been described above for purposes of illustration, it will be evident to those skilled in the art that numerous variations of the details of the present invention may be made without departing from the invention as defined in the appended claims.

What is claimed is:

1. An apparatus for capturing and retrieving embolic material from a blood vessel, the apparatus comprising:
   a first hollow tube having a proximal end and a distal end having inflation apertures, wherein the distal end is insertable into the vessel;
   a second hollow tube coaxially and slidably positioned over the first hollow tube, wherein a wall of the second hollow tube includes a plurality of aspiration apertures structured and configured for retrieving the embolic material;
   a seal preventing fluid communication between the inflation apertures of the first hollow tube and the aspiration apertures at the distal end of the second hollow tube; and
   a radially expandable segment expandable from a deflated position to an inflated position in contact with an inner wall of the blood vessel structured and configured for capturing the embolic material to be retrieved, wherein a proximal portion of the radially expandable segment is attached to the second hollow tube at a position distal to the aspiration apertures, and a distal portion of the radially expandable segment is attached to the first hollow tube at a position distal to the inflation apertures.

2. The apparatus of claim 1, wherein the second hollow tube is structured to be coaxially advanced toward the proximal end of the first hollow tube to a storage position when the radially expandable segment is in the deflated position.

3. The apparatus of claim 2, wherein the radially expandable segment is structured to compactly surround at least a portion of the first hollow tube and at least a portion of the second hollow tube when the second hollow tube is in the storage position.

4. The apparatus of claim 3, further comprising means for maintaining tension on the radially expandable segment when the second hollow tube is in the storage position.

5. The apparatus of claim 4, wherein the radially expandable segment is elongated when the tension is maintained thereon.

6. The apparatus of claim 4, wherein the tension is maintained on the radially expandable segment by an o-ring seal mounted between the first and second hollow tubes which provides frictional resistance to relative movement of the first and second hollow tubes.

7. The apparatus of claim 2, wherein the diameter of the radially expandable segment is from about 0.8 mm to about 3 mm when the radially expandable segment is in the deflated position and the second hollow tube is in the storage position.

8. The apparatus of claim 2, wherein the diameter of the radially expandable segment is from about 0.85 mm to about 1.4 mm when the radially expandable segment is in the deflated position and the second hollow tube is in the storage position.

9. The apparatus of claim 2, wherein the length of the radially expandable segment is from about 0.25 cm to about 8 cm when the radially expandable segment is in the deflated position and the second hollow tube is in the storage position.

10. The apparatus of claim 2, wherein the length of the radially expandable segment is from about 1 cm to about 4 cm when the radially expandable segment is in the deflated position and the second hollow tube is in the storage position.

11. The apparatus of claim 1, wherein the second hollow tube is structured to be coaxially advanced towards the distal end of the first hollow tube to a treatment position when the radially expandable segment is in an inflated position.

12. The apparatus of claim 11, wherein the diameter of the radially expandable segment is from about 2 mm to about 30 mm when the radially expandable segment is in the inflated position and the second hollow tube is in the treatment position.

13. The apparatus of claim 11, wherein the diameter of the radially expandable segment is from about 3 mm to about 11 mm when the radially expandable segment is in the inflated position and the second hollow tube is in the treatment position.

14. The apparatus of claim 11, wherein the ratio of the diameter of the radially expandable segment in the inflated position when the second hollow tube is in the treatment position to the diameter of the radially expandable segment in a deflated position when the second hollow tube is in a storage position is from about 2.5:1 to about 10:1.

15. The apparatus of claim 11, wherein the ratio of the diameter of the radially expandable segment in the inflated position when the second hollow tube is in the treatment position to the diameter of the radially expandable segment in a deflated position when the second hollow tube is in a storage position is from about 3.5:1 to about 8:1.

16. The apparatus of claim 11, wherein the length of the radially expandable segment is from about 0.25 cm to about 4 cm when the radially expandable segment is in the inflated position and the second hollow tube is in the treatment position.

17. The apparatus of claim 11, wherein the length of the radially expandable segment is from about 0.5 cm to about 2 cm when the radially expandable segment is in the inflated position and the second hollow tube is in the treatment position.

18. The apparatus of claim 1, wherein a wall of the first hollow tube comprises a plurality of apertures inside the radially expandable segment.

19. The apparatus of claim 1, wherein the distal end of the first hollow tube comprises a flexible material.

20. The apparatus of claim 19, wherein the distal portion of the radially expandable segment is aff ached to the flexible material.

21. The apparatus of claim 1, wherein the second hollow tube comprises a guidewire.

22. The apparatus of claim 21, wherein the guidewire comprises coiled wire.

23. The apparatus of claim 1, wherein the second hollow tube is structured and arranged to receive a treatment device for treating the blood vessel.

24. The apparatus of claim 1, further comprising a hub at the proximal end of the apparatus in communication with the first hollow tube and the second hollow tube.

25. The apparatus of claim 24, wherein the hub is removeably attached to the first hollow tube and the second hollow tube.

26. An apparatus for capturing and retrieving embolic material from a blood vessel, the apparatus comprising:
   a first hollow tube having a proximal end and a distal end having inflation apertures, wherein the distal end is insertable into the vessel;
   a second hollow tube coaxially positioned over the first hollow tube, wherein a wall of the second hollow tube includes a plurality of aspiration apertures structured and configured for retrieving the embolic material;

a radially expandable segment attached to the first hollow tube at a position distal to the inflation apertures and the second hollow tube at a position distal to the aspiration apertures and structured and configured for capturing the embolic material to be retrieved;

a seal preventing fluid communication between the inflation apertures and the aspiration apertures at the distal end of the second hollow tube; and means for compactly surrounding at least a portion of the first hollow tube and at least a portion of the second hollow tube with the radially expandable segment.

* * * * *

UNITED STATES PATENT AND TRADEMARK OFFICE
CERTIFICATE OF CORRECTION

| | | |
|---|---|---|
| PATENT NO. | : 7,322,958 B2 | Page 1 of 1 |
| APPLICATION NO. | : 10/329585 | |
| DATED | : January 29, 2008 | |
| INVENTOR(S) | : Mark H. Wholey and Michael Wholey | |

It is certified that error appears in the above-identified patent and that said Letters Patent is hereby corrected as shown below:

Column 10, Line 45, Claim 20
The apparatus of claim 19, wherein the distal portion of the radially expandable segment is "aff ached" -- attached -- to the flexible material.

Signed and Sealed this

Seventh Day of July, 2009

JOHN DOLL
*Acting Director of the United States Patent and Trademark Office*